US008145289B2

(12) United States Patent
Calabro' et al.

(10) Patent No.: US 8,145,289 B2
(45) Date of Patent: Mar. 27, 2012

(54) ESOPHAGEAL ELECTROCATHETER

(75) Inventors: Alberto Calabro', Vicchio (IT);
Pasquale Del Bene, Vicchio (IT)

(73) Assignee: Fiab S.p.A., Vicchio (IT)

( * ) Notice: Subject to any disclaimer, the term of this patent is extended or adjusted under 35 U.S.C. 154(b) by 1106 days.

(21) Appl. No.: 11/996,041

(22) PCT Filed: Jul. 19, 2006

(86) PCT No.: PCT/IB2006/002049
§ 371 (c)(1),
(2), (4) Date: Jan. 17, 2008

(87) PCT Pub. No.: WO2007/010386
PCT Pub. Date: Jan. 25, 2007

(65) Prior Publication Data
US 2008/0215047 A1    Sep. 4, 2008

(30) Foreign Application Priority Data

Jul. 22, 2005 (IT) .............................. BO2005A0495

(51) Int. Cl.
*A61B 5/04*        (2006.01)
*A61B 5/01*        (2006.01)
*A61B 18/14*       (2006.01)
(52) U.S. Cl. ........................... 600/380; 600/549; 606/41
(58) Field of Classification Search ................. 600/380, 600/549; 606/41
See application file for complete search history.

(56) References Cited

U.S. PATENT DOCUMENTS

| | | | | |
|---|---|---|---|---|
| 4,559,046 A * | 12/1985 | Groshong et al. | ............ | 604/524 |
| 5,343,860 A * | 9/1994 | Metzger et al. | ................ | 600/380 |
| 5,623,940 A | 4/1997 | Daikuzono | | |
| 6,258,087 B1 | 7/2001 | Edwards et al. | | |
| 6,273,886 B1 | 8/2001 | Edwards et al. | | |
| 6,325,798 B1 | 12/2001 | Edwards et al. | | |
| 6,355,031 B1 | 3/2002 | Edwards et al. | | |
| 6,358,245 B1 | 3/2002 | Edwards et al. | | |
| 6,423,058 B1 | 7/2002 | Edwards et al. | | |
| 6,438,400 B1 * | 8/2002 | Beard et al. | ................... | 600/380 |
| 6,464,697 B1 | 10/2002 | Edwards et al. | | |
| 2002/0013581 A1 | 1/2002 | Edwards et al. | | |
| 2002/0156470 A1 | 10/2002 | Shadduck | | |
| 2003/0045871 A1 | 3/2003 | Jain et al. | | |
| 2005/0033271 A1 | 2/2005 | Qin et al. | | |
| 2006/0106375 A1 | 5/2006 | Werneth et al. | | |

FOREIGN PATENT DOCUMENTS

WO    WO 99/42047 A1    8/1999
WO    WO 2006/055286 A2    5/2006

* cited by examiner

*Primary Examiner* — Lee Cohen
(74) *Attorney, Agent, or Firm* — Pearne & Gordon LLP

(57) ABSTRACT

An esophageal catheter comprises an insertion element (1) able to be inserted into a patient's esophagus and having a distal end (2) and a sheath (3) containing the cables (7) for connection to at least two temperature sensors (4) fitted along the element (1) in the vicinity of the distal end, the sensors being mounted in predetermined positions relative to one or more positioning elements (5, 6) defining a temperature detection zone (8).

13 Claims, 1 Drawing Sheet

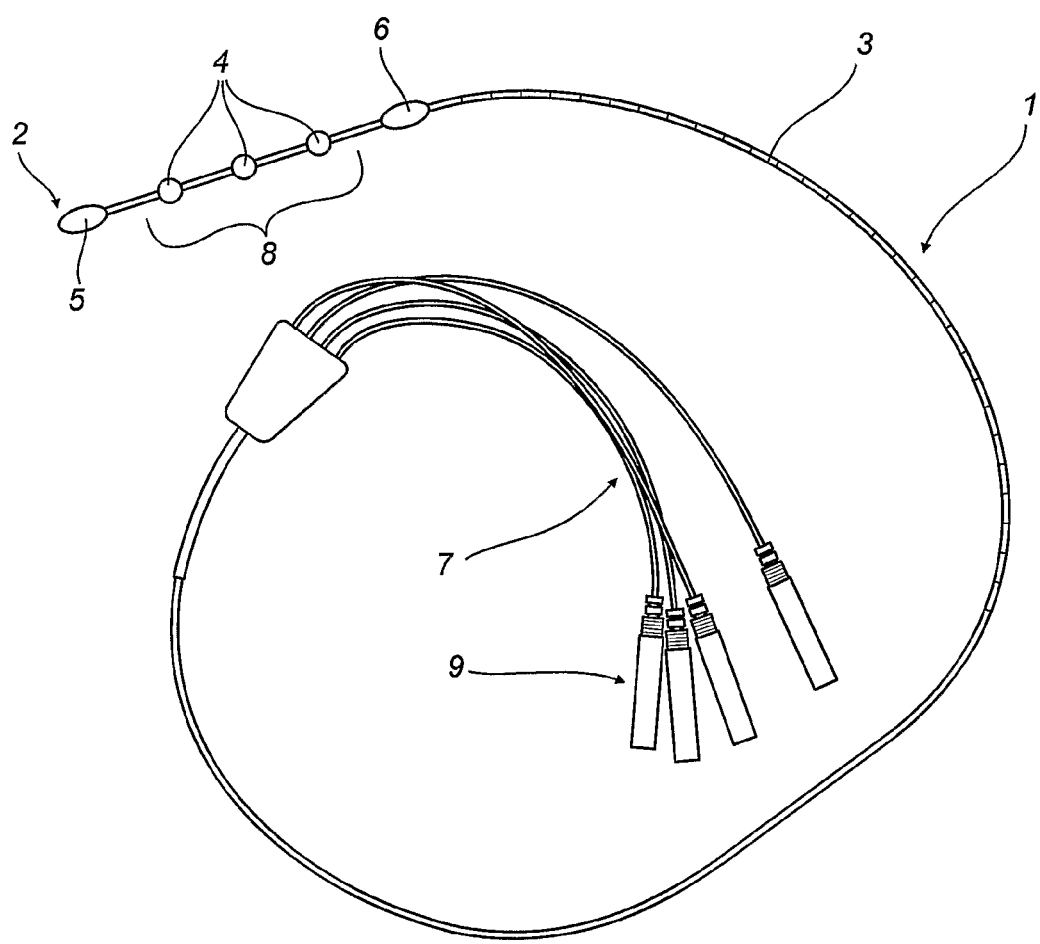

ESOPHAGEAL ELECTROCATHETER

TECHNICAL FIELD

This invention relates to an esophageal electrocatheter for use in cardiac ablation operations.

BACKGROUND ART

It is known that some disorders, such as atrial fibrillation in particular, are treated by ablation techniques whereby radio frequency irradiations are applied to the heart tissue (in particular to the atrial walls) in order to restore normal functioning of the electrical conduction of the heart and reduce the occurrence of fibrillation.

These techniques therefore use a source of radio frequency energy which, besides performing the function just mentioned, involve heating the offending tissue and the tissue of the surrounding areas.

It is also known that in some circumstances, repeated and excessive heating of the tissue concerned causes swellings which, over time, may lead to necrosis putting the patient's health at serious risk.

At present, the heating level reached during cardiac ablation operations is controlled with the aid of complex mathematical modelling techniques used to create temperature maps of the treated areas.

These techniques are, however, not only extremely complex and expensive but also indirect, that is to say, they are not based on direct measurement of the temperature at the specific point affected by the risk of fistula.

DISCLOSURE OF THE INVENTION

This invention therefore has for an aim to provide a device that overcomes the drawbacks of prior art in a simple and reliable manner, and reduces the level of risk for patients undergoing cardiac ablation treatments.

The invention takes advantage of the fact that in many people the left atrial wall tissue is in contact with or very close to the esophageal lumen. It may thus be assumed that the temperature is propagated from the atrial tissue to the esophagus wall, making it possible to measure the atrial temperature through the esophagus.

The above mentioned aims are therefore substantially achieved by an esophageal catheter comprising the characteristics described in one or more of the appended claims.

DESCRIPTION OF THE DRAWINGS

Further characteristics and advantages of the invention are more apparent in the non-limiting description of a preferred embodiment of it, as illustrated in the accompanying drawing, in which:

FIG. 1 illustrates a catheter according to the invention.

DETAILED DESCRIPTION OF THE PREFERRED EMBODIMENTS OF THE INVENTION

With reference to the accompanying drawing, a catheter according to the invention comprises a flexible insertion element 1, including a sheath 3 that terminates with a distal end 2.

In the vicinity of or at the distal end 2, there are reference elements 5, 6 which define a zone 8 where the temperature may be detected and/or monitored by one or more temperature sensors 4.

In the embodiment described, there are three temperature sensors 4 which can detect a central value and the deviation from this value at two symmetrical, equidistant points.

Preferably, the sensors consist of thermocouples whose connecting cables 7 run inside the sheath 3 and terminate outside it with connectors 9 for connection to an external control unit that is not shown in the drawing.

As shown in FIG. 1, there are three temperature sensors (4). These three temperature sensors include a first temperature sensor positioned a first distance from the distal end, a second temperature sensor positioned a second distance from the distal end, and a third temperature sensor positioned a third distance from the distal end. As shown in FIG. 1, the first distance is shorter than the second distance, and the second distance is shorter than the third distance. As shown in FIG. 1, the portion of the catheter between the first temperature sensor and the third temperature sensor consists of (a) a first portion of the sheath (3) between the first temperature sensor and the second temperature sensor, (b) the second temperature sensor, and (c) a second portion of the sheath (3) between the second temperature sensor and the third temperature sensor. As shown in FIG. 1, each of the first, second and third temperature sensors has a lateral dimension greater than any lateral dimension of the first portion and the second portion of the sheath (3).

Also preferably, the elements 5, 6 consist of X-ray traceable parts enabling the monitoring zone 8 to be positioned along the esophagus after insertion of the catheter according to radiological practice.

For example, the elements 5, 6 might consist of metal parts (such as electrodes) or traces of X-ray dye.

In another embodiment, the elements 5, 6 might consist of platinum or steel rings which, besides being X-ray traceable, can serve the purpose of electrodes connected to the cables 7 for recording the electrical potentials emitted by the muscular atrial walls in such a way as to identify the point where the temperature sensors are optimally contiguous with the atrial wall.

Alternatively, the element 5, 6 might also be made as reference points on a metric scale on the sheath.

In this case, the sensors 4 are positioned by following the inserted length of the catheter and calculating the measurement shown on the sheath.

In operation, the catheter 1 is connected to an external control unit which detects the temperature values read by the sensors 4, while the position of the catheter during insertion into the patient's esophagus is followed either radiologically, if the elements 5, 6 are of the X-ray traceable type, or according to the inserted catheter length readable from the metric scale on the sheath 3.

When the catheter is in position and the monitoring zone 8 corresponds with the part of the esophagus contiguous with the myocardial wall to be treated, ablation may start.

During the operation, the radiofrequency waves emitted by the ablation unit cause local heating which is read by the sensors 4 and sent to the control unit outside the body.

Using appropriate algorithms, the temperature values detected are processed by the control unit and used to emit an audible alarm to alert the operator when a critical temperature is reached.

Preferably, the control unit is therefore connected to the catheter for automatically controlling the levels of temperature and energy emitted during the operation, thus constituting a cardiac ablation apparatus providing a feedback signal for controlling the operation.

The apparatus may also comprise devices for displaying the temperature pattern and visual or audible alarms activated automatically when a preset value of critical temperature is reached.

The invention described has evident industrial applications and can be modified and adapted in several ways without thereby departing from the scope of the inventive concept. Moreover, all details of the invention may be substituted by technically equivalent elements.

The invention claimed is:

1. An esophageal catheter comprising an insertion element (1) able to be inserted into a patient's esophagus and having a distal end (2) and a sheath (3) containing cables (7) connected to at least three temperature sensors (4) fitted along the element (1) in the vicinity of the distal end, the sensors being mounted in predetermined positions relative to one or more positioning elements (5, 6) fixed along the element (1) and defining a temperature detection zone (8), the three temperature sensors being a first temperature sensor positioned a first distance from the distal end, a second temperature sensor positioned a second distance from the distal end, and a third temperature sensor positioned a third distance from the distal end, the first distance being shorter than the second distance, the second distance being shorter than the third distance;

the portion of the catheter between the first temperature sensor and the third temperature sensor consisting of (a) a first portion of the sheath (3) between the first temperature sensor and the second temperature sensor, (b) the second temperature sensor, and (c) a second portion of the sheath (3) between the second temperature sensor and the third temperature sensor, each of the first, second and third temperature sensors having a lateral dimension greater than any lateral dimension of the first portion and the second portion of the sheath (3); the first portion of the sheath (3) being the same length as the second portion of the sheath (3) so that the three temperature sensors can detect a central value and two deviations from the central value at two symmetrical, equidistant points.

2. The catheter according to claim 1, wherein the positioning elements are X-ray traceable elements whose trace can be detected outside the body.

3. The catheter according to claim 2, wherein the X-ray traceable positioning elements are metal electrodes for recording an electrical potential.

4. The catheter according to claim 2 wherein the X-ray traceable positioning elements consist of traces of X-ray dye.

5. The catheter according to claim 1, wherein the sheath has a metric scale and the positioning elements consist of points on the catheter located at a predetermined distance from the temperature sensors.

6. The catheter according to claim 1, wherein the temperature sensors consist of thermocouples or thermistors.

7. The catheter according to claim 1, wherein the positioning elements are X-ray traceable elements.

8. The catheter according to claim 1, wherein the temperature sensors are three in number.

9. A cardiac ablation apparatus, comprising an ablation unit equipped with radiofrequency emitting electrodes, a catheter according to claim 1, and a unit for controlling the apparatus, for enabling/disabling radiofrequency emission upon reaching one or more predetermined temperature values detected by the catheter.

10. The apparatus according to claim 9, comprising a unit for radiologically detecting the position of the positioning elements.

11. The apparatus according to claim 9, comprising devices for displaying the temperature pattern detected by the sensors (4).

12. The apparatus according to claim 9, comprising a visual and/or audible alarm activated automatically when a preset value of critical temperature is reached.

13. A method of using a catheter according to claim 1 comprising the steps of: inserting the catheter into a patient's esophagus and then monitoring a cardiac ablation procedure in the patient via the catheter's temperature sensors.

* * * * *